United States Patent
Sage-Passant (10) Patent No.: US 10,610,910 B2
(45) Date of Patent: Apr. 7, 2020

(54) WASTE DISPOSAL APPARATUS AND METHOD

(71) Applicant: Mechline Developments Limited, Milton Keynes (GB)

(72) Inventor: Peter Sage-Passant, Milton Keynes (GB)

(73) Assignee: Mechline Developments Limited (GB)

( * ) Notice: Subject to any disclaimer, the term of this patent is extended or adjusted under 35 U.S.C. 154(b) by 421 days.

(21) Appl. No.: 15/305,908

(22) PCT Filed: Jan. 20, 2015

(86) PCT No.: PCT/GB2015/050120
§ 371 (c)(1),
(2) Date: Oct. 21, 2016

(87) PCT Pub. No.: WO2015/162397
PCT Pub. Date: Oct. 29, 2015

(65) Prior Publication Data
US 2017/0043383 A1   Feb. 16, 2017

(30) Foreign Application Priority Data

Apr. 24, 2014   (GB) .................................. 1407229.2

(51) Int. Cl.
*B09B 3/00*   (2006.01)
*B09B 5/00*   (2006.01)
(Continued)

(52) U.S. Cl.
CPC .................. *B09B 3/00* (2013.01); *B09B 5/00* (2013.01); *C12M 21/16* (2013.01); *C12M 29/00* (2013.01); *C12M 41/44* (2013.01); *C12M 41/48* (2013.01)

(58) Field of Classification Search
CPC ...... C12M 21/02; C12M 37/00; C12M 39/00; C12M 41/48; C12M 23/38; C12M 23/22;
(Continued)

(56) References Cited

U.S. PATENT DOCUMENTS

| | | | | |
|---|---|---|---|---|
| 5,004,459 A | * | 4/1991 | Peabody | A61M 1/28 604/29 |
| 2014/0356932 A1 | * | 12/2014 | Sage-Passant | B09B 3/00 435/262 |

FOREIGN PATENT DOCUMENTS

| | | |
|---|---|---|
| GB | 2495992 A | 5/2013 |
| JP | H09-29211 | 2/1997 |

(Continued)

OTHER PUBLICATIONS

International Search Report dated Mar. 11, 2015 for International application No. PCT/GB2015/050120.
(Continued)

*Primary Examiner* — William H. Beisner
*Assistant Examiner* — Danielle B Henkel
(74) *Attorney, Agent, or Firm* — Fay Sharpe LLP (57) ABSTRACT

A waste disposal apparatus for disposing of waste materials using aerobic decomposition includes a decomposition chamber, a waste inlet configured to admit waste materials into the decomposition chamber, a water feed system configured for supplying feed water to the decomposition chamber and a drain system configured for draining drain liquid from the decomposition chamber. The apparatus also includes a sensing system configured to sense the volume VF of feed water supplied to the decomposition chamber and the volume VD of drain liquid drained from the decomposition chamber, and a computing device that is configured
(Continued)

Waste 2-0 machine with side panel removed and cut-away section of tank to determine the quantity of waste material processed by the waste disposal apparatus from the sensed volumes VF and VD.

26 Claims, 6 Drawing Sheets

(51) Int. Cl.
| | |
|---|---|
| *C12M 1/16* | (2006.01) |
| *C12M 1/00* | (2006.01) |
| *C12M 1/34* | (2006.01) |
| *C12M 1/36* | (2006.01) |

(58) Field of Classification Search
CPC ...... C12M 29/06; C12M 31/08; C12M 33/00; C12M 41/00; C12M 29/00; C12M 41/44; C12M 21/16; B09B 3/00; B09B 5/00
See application file for complete search history.

(56) References Cited

FOREIGN PATENT DOCUMENTS

| | | |
|---|---|---|
| JP | H11128888 | 5/1999 |
| JP | 2006-198521 | 8/2006 |
| KR | 2007 0032509 | 3/2007 |
| KR | 10 0839377 | 6/2008 |
| KR | 2010 0073770 | 7/2010 |
| KR | 10-2011-0013938 | 2/2011 |
| WO | WO 2008/150059 A1 | 12/2008 |

OTHER PUBLICATIONS

Written Opinion dated Mar. 11, 2015 for International application No. PCT/GB2015/050120.
British Search Report dated Oct. 21, 2014 for Application No. GB1407229.2.
International Preliminary Report on Patentability dated Oct. 25, 2016 for International application No. PCT/GB2015/050120.

* cited by examiner

WASTE DISPOSAL APPARATUS AND METHOD

FIELD OF INVENTION

The present invention relates to a waste disposal apparatus and in particular but not exclusively to a waste disposal apparatus for disposing of unwanted food waste using aerobic decomposition. The invention also relates to a method of disposing of waste materials using aerobic decomposition.

BACKGROUND

Aerobic decomposition is a well-known method for disposing of unwanted food waste. It is useful in that it diverts food waste from landfill, which is generally agreed to be expensive, environmentally unfriendly and unsustainable.

Food security is a growing issue all over the World, and many Governments have made reducing food waste from domestic and commercial premises a priority in a bid to combat the growing threat. In addition, disposal of food waste can be difficult and expensive and a reduction in food waste levels has a direct impact on disposal costs, and on the environment. Food waste has a very high embedded energy cost, because often it has been grown, stored, transported, processed, packaged, refrigerated and cooked before being thrown away. Any method of reducing food waste therefore has a positive and direct impact on the environment.

Commercial foodservice operations often generate high levels of food waste. It is extremely difficult to efficiently and accurately measure levels of food waste because of the relatively high volumes involved, and without accurate information it is very difficult for foodservice operators to take corrective action appropriate to their specific application. Reducing food waste in an army kitchen can be very different from reducing waste in a hospital, for example.

Where food waste is stored in commercial operations for weekly collection, it is extremely difficult to determine each individual day's food waste rates without relying on an operator manually weighing and recording each load prior to disposal, which is expensive, time-consuming and open to error. Some waste collection vehicles have inbuilt weighing devices to monitor the loads collected, but these can be inaccurate and cannot distinguish between individual days' loads unless daily collections are undertaken, which is expensive, inconvenient, environmentally unfriendly, and counterproductive. Where food waste is disposed of by maceration, there is no means of monitoring food waste levels other than weighing and recording each load prior to maceration. This is also expensive, time-consuming and open to error.

Many food service operations use food waste digester machines to dispose of their food waste. The benefits of monitoring food waste by passing it through a food waste digester machine include the fact that it requires no additional time or effort on behalf of the operator, and the monitoring device cannot be bypassed, as in most operations the food waste digester machine provides the only means of food waste disposal.

Some food waste digester machines incorporate load sensing devices that weigh the food waste placed in the device by sensing the gross weight of the device and food waste, and then subtracting the net weight of the device. The problem with this type of device is that it cannot distinguish between food waste and contaminants like bones, cutlery, crockery, packaging etc., which can be erroneously placed in the device. It is also common for items to be placed on top of the machines or for operators to lean on the machines when loading. Food waste digester machines invariably use water as part of the digestion process, and it is not possible to accurately calculate the rates at which different foodstuffs absorb water prior to being digested. All of the above add to the inaccuracies of these devices.

SUMMARY OF THE INVENTION

It is an object of the present invention to provide a waste disposal apparatus that mitigates one or more of the disadvantages described above.

Another object of the present invention to provide the foodservice operator with the means to measure and monitor each day's food waste levels by incorporating a food waste volume sensing device into the operator's food waste digester machine, which is not affected by the problems associated with other devices as outlined above.

Food waste from a commercial foodservice operation is inevitable, and may consist of some or all of the following: Raw food from preparation, over-provisioning or food becoming out of date, cooked food waste from plate waste or from over provisioning. Accurate waste information provides operators of the food waste digester machines with the ability to accurately track food waste rates from their facility and to take corrective action by monitoring peaks and troughs of food waste levels, and to relate this directly back to their daily menu items and operation.

According to one aspect of the present invention there is provided a waste disposal apparatus for disposing of waste materials using aerobic decomposition, the apparatus including a decomposition chamber, a waste inlet configured to admit waste materials into the decomposition chamber, a water feed system configured for supplying feed water to the decomposition chamber, a drain system configured for draining drain liquid from the decomposition chamber, a sensing system configured to sense the volume VF of feed water supplied to the decomposition chamber and the volume VD of drain liquid drained from the decomposition chamber, and a computing device that is configured to determine the quantity of waste material processed by the apparatus from the sensed volumes VF and VD.

The waste disposal apparatus allows the operator to determine accurately and efficiently the quantity of waste material processed by the apparatus. This allows operators to monitor and adapt their processes to minimize food waste, thereby providing environmental and operational benefits. Another advantage of the apparatus is that it avoids a number of other problems associated with conventional waste digester machines, such as their inability to distinguish between food waste and contaminants accidentally placed in the decomposition chamber, and their sensitivity to external loads applied to the apparatus.

Advantageously, the computing device is configured to determine the weight W of waste material processed by the waste disposal apparatus using the algorithm $W=(VD-VF) \div k$ where k has a value in the range 0.7-0.8, preferably about 0.75. This algorithm makes it very easy to determine the weight W of waste material processed by the waste disposal apparatus from just two simple measurements.

Advantageously, the drain system includes a drain pump, and the volume VD of drain liquid drained from the decomposition chamber is determined by sensing the number of times Nd the drain pump is fired and multiplying this value by the drain pump volume Vd. This makes it possible to measure the volume VD of drain liquid drained from the decomposition chamber, without measuring the amount of liquid directly. Only the number of times the drain pump has been fired needs to be monitored, and this number can be counted very easily by sensing operating signals sent to the drain pump, or signals received from the sensing system. Alternatively, the volume VD of drain liquid can be measured by any conventional fluid measuring technique, for example by using a flow meter or gauge.

Advantageously, the drain system includes a level sensing device that senses an accumulation of drain liquid in the decomposition chamber, and wherein the drain pump is configured to fire when the accumulation of drain liquid reaches a predetermined level, the drain pump volume Vd being regulated by the volume of the accumulation of drain liquid when the drain pump is fired.

Advantageously, the feed system includes a feed pump, and the volume VF of feed water supplied to the decomposition chamber is determined by sensing the number of times Nf the feed pump is fired and multiplying this value by the feed pump volume Vf. This makes it possible to measure the volume VF of feed water supplied to the decomposition chamber, without measuring the amount of water directly. Only the number of times the feed pump has been fired needs to be monitored, and this number can be counted very easily by sensing operating signals sent to the feed pump, or signals received from the sensing system. Alternatively, the volume VF of feed water can be measured by any conventional fluid measuring technique, for example by using a flow meter or gauge.

Advantageously, the feed system includes a water tank from which feed water is drawn by the feed pump, and the feed pump volume Vf is regulated by the volume of the water tank. This makes it very easy to regulate the feed pump volume accurately and consistently.

Advantageously, the water tank includes high and low water level sensors, and water is supplied to the water tank via a valve that opens and closes in response to signals received from the high and low water level sensors. This also helps with regulating the feed pump volume.

Advantageously, the waste disposal apparatus includes a control system that is configured to receive signals from the sensing system and control operation of the water feed system and the drain system in response to signals received from the sensing system.

Advantageously, the control system includes a data storage device for storing data relating to operation of the waste disposal apparatus.

Advantageously, the control system includes an output device for providing output data relating to operation of the waste disposal apparatus. The output device may be configured to control operation of a display device, or to transmit output data to a wireless transmitter, a data router or a socket for a wired connection, allowing output data to be transferred to an external device (for example, a laptop or tablet computer).

The apparatus can be used for the disposal of biodegradable waste materials, for example food waste. This allows the waste materials to be disposed of easily, quickly and hygienically and avoids the environmental and economic disadvantages associated with disposing of those waste materials in landfill sites.

Advantageously, the waste disposal apparatus includes a dosing system for automatically dosing waste material in the decomposition chamber with a working fluid. This ensures that the working fluid is applied effectively and at the correct times, and that the quantity of working fluid used is controlled to avoid wastage.

Preferably, the dosing system includes a bag-in-box supply of working fluid, in which the working fluid is contained within a flexible polymeric bag within a rigid box-like container made, for example, of cardboard. This is a very convenient way to store the working fluid and it allows the supply of working fluid to be replenished easily and quickly. Degradation of the working fluid while in storage is also reduced, since the bag of the bag-in-box container is hermetically sealed.

Advantageously, the dosing system is constructed and arranged to deliver a predetermined quantity of working fluid to the decomposition chamber each time the closure member is opened. Advantageously, the working fluid includes a blend of bacteria, free enzymes and plant extracts.

Advantageously, the decomposition chamber and optionally the closure member are made substantially or wholly of a polymeric material, optionally polyethylene. This improves the thermal insulation of the decomposition chamber, thus reducing or eliminating the need for external heating (some heat being generated by decomposition of the waste materials). If heating is required, this can be provided using a low power heating unit, thus reducing the energy demands of the apparatus.

The use of polymeric materials considerably reduces the weight and possibly also the size of the apparatus. It is therefore possible to design the apparatus as a mobile unit and it relatively easy to relocate the apparatus when required. The moulded components are also less likely to leak than traditional welded metal components, and they are easy to clean and maintain.

The decomposition chamber and optionally the closure member are preferably rotationally moulded components, this manufacturing process being particularly suitable for large components of this type as it allows large wall thicknesses to be formed, which increase the level of thermal insulation. The use of moulded polymeric components is also very cost effective as compared for example to stainless steel components.

The waste disposal apparatus may include a heater for heating the decomposition chamber. The heater is preferably thermostatically controlled and it may for example consist of a low power heat mat that is attached to the base of the decomposition chamber.

According to another aspect of the invention there is provided a method of disposing of waste materials using aerobic decomposition, the method including loading waste materials into a decomposition chamber method of disposing of waste materials using aerobic decomposition, the method including loading waste materials into a decomposition chamber, supplying feed water to the decomposition chamber, draining drain liquid from the decomposition chamber, sensing the volume VF of feed water supplied to the decomposition chamber and the volume VD of drain liquid drained from the decomposition chamber, and determining the quantity of waste material processed by the waste disposal apparatus from the sensed volumes VF and VD.

Advantageously, the method includes determining the weight W of waste material processed by the waste disposal apparatus using the algorithm $W=(VD-VF) \div k$ where k has a value in the range 0.7-0.8, preferably about 0.75.

Advantageously, the method includes determining the volume VD of drain liquid drained from the decomposition chamber by sensing the number of times Nd a drain pump is fired and multiplying this value by the drain pump volume Vd.

Advantageously, the method includes sensing an accumulation of drain liquid in the decomposition chamber, and firing the drain pump when the accumulation of drain liquid reaches a predetermined level, the drain pump volume Vd being regulated by the volume of the accumulation of drain liquid when the drain pump is fired.

Advantageously, the method includes determining the volume VF of feed water supplied to the decomposition chamber by sensing the number of times Nf a feed pump is fired and multiplying this value by the feed pump volume Vf.

Advantageously, the method includes drawing feed water from a water tank using the feed pump, and regulating the feed pump volume Vf by the volume of the water tank.

Advantageously, the method includes supplying feed water to the water tank via a valve and controlling the valve so that it opens and closes in response to signals received from high and low water level sensors in the water tank.

Advantageously, the method includes receiving signals from the sensing system and controlling operation of the water feed system and the drain system in response to signals received from the sensing system.

Advantageously, the method includes storing data relating to operation of the waste disposal apparatus in a data storage device.

Advantageously, the method includes providing output data relating to operation of the waste disposal apparatus.

Advantageously, the waste materials are disposed of by aerobic decomposition, in which the waste materials are placed in the decomposition chamber, a working fluid that includes a blend of bacteria, free enzymes and plant extracts is applied to the waste materials, the waste materials are stirred to encourage aerobic decomposition thereof, and decomposed waste materials are discharged from the chamber.

The waste materials are preferably waste food products.

Advantageously, the method is implemented using an apparatus according to any one of the preceding statements of invention.

Advantageously, the waste materials are disposed of by aerobic decomposition, in which the waste materials are placed in the decomposition chamber, a working fluid that includes a blend of bacteria, free enzymes and plant extracts is applied to the waste materials, the waste materials are stirred to encourage aerobic decomposition thereof, and decomposed waste materials are discharged from the chamber. The waste materials may for example be waste food products.

The method is preferably implemented using an apparatus according to any one of the preceding statements of invention.

BRIEF DESCRIPTION OF THE DRAWINGS

Certain embodiments of the invention will now be described by way of example with reference to the accompanying drawings, in which.

DETAILED DESCRIPTION OF THE DRAWINGS

Figure 1:
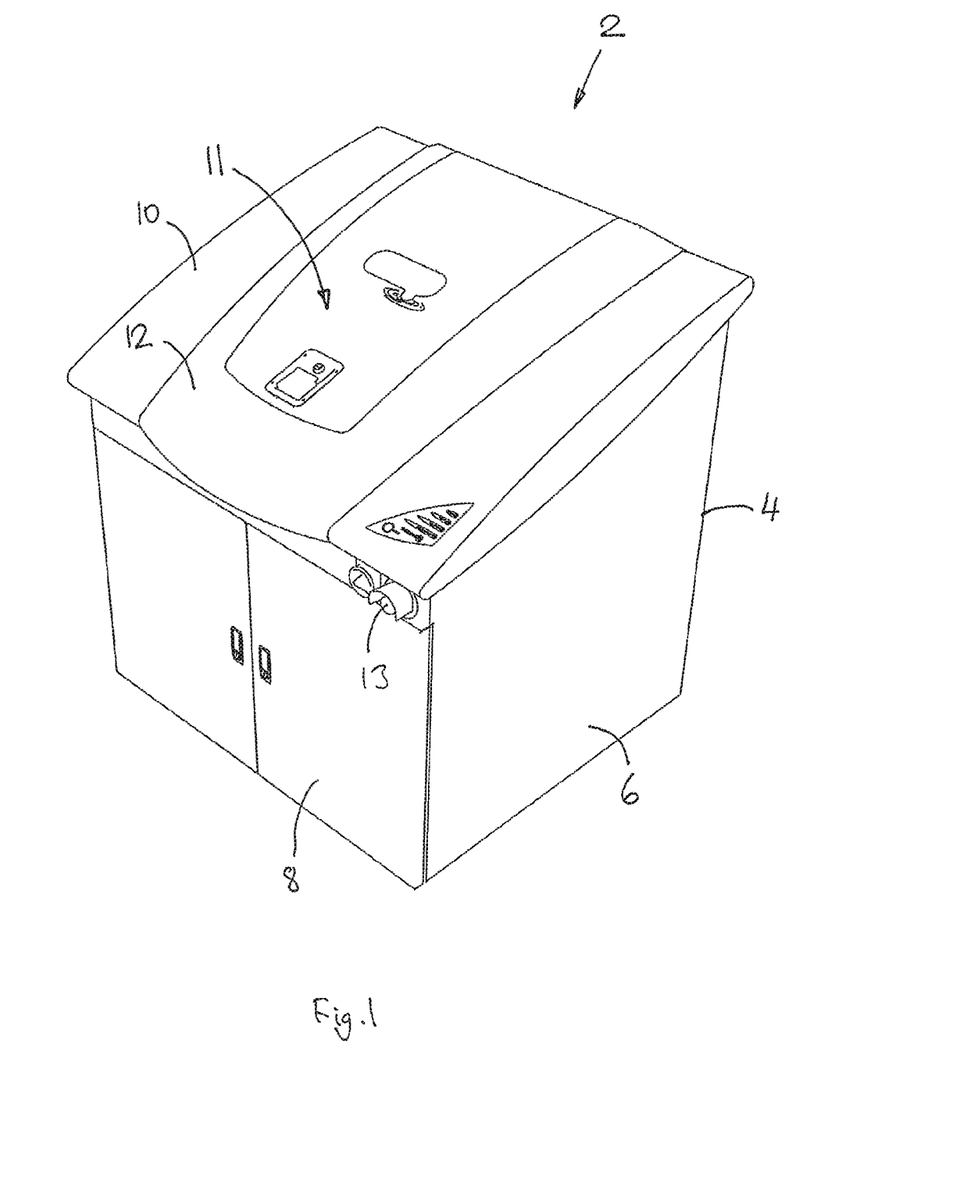
FIG. 1 is an isometric view of a waste disposal machine from the right side.
Figure 2:
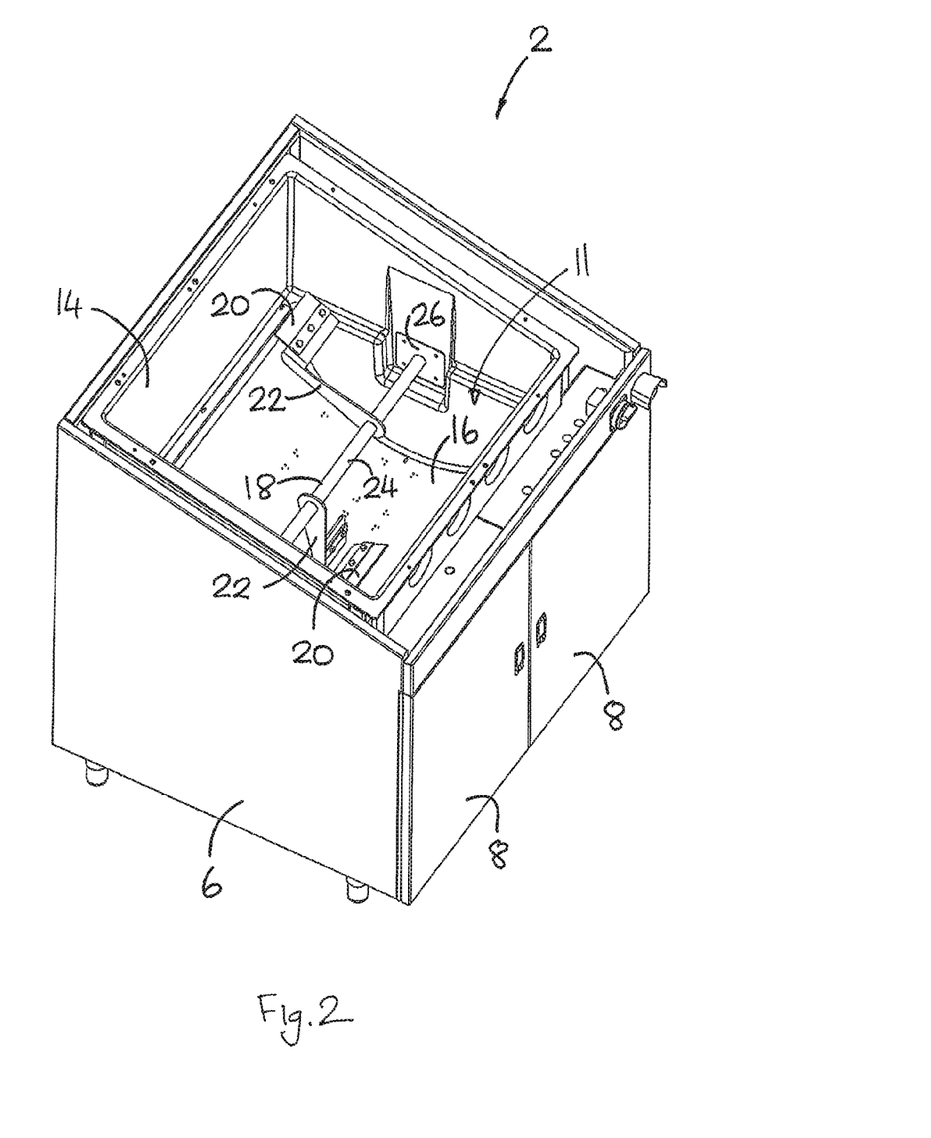
FIG. 2 is an isometric view of the waste disposal machine from the left side, with the top removed.
Figure 3:
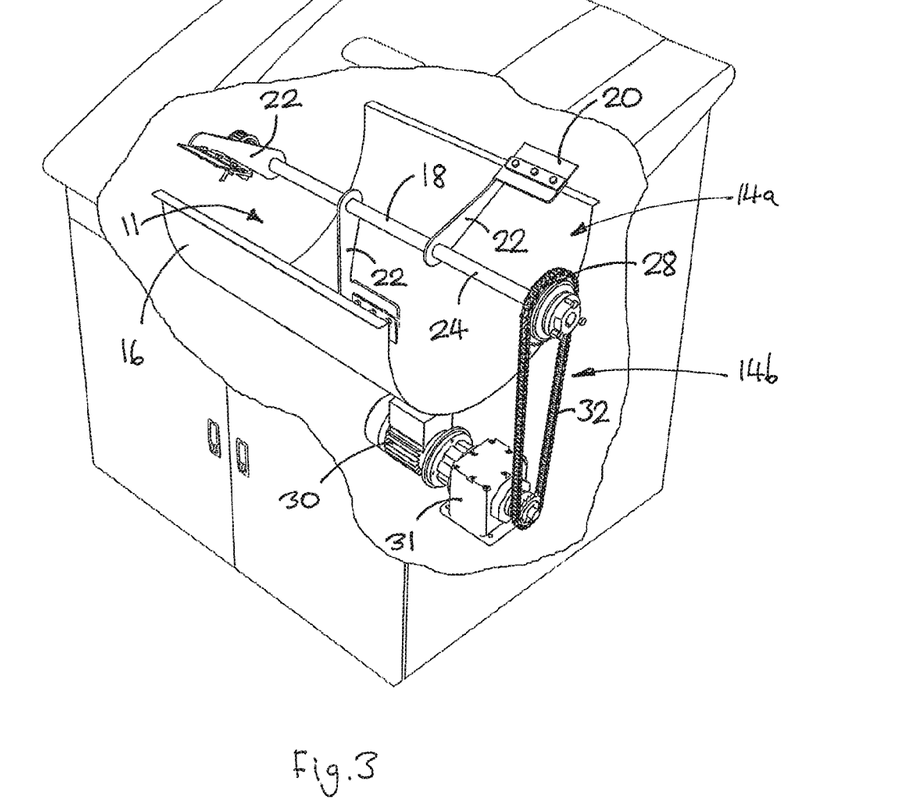
FIG. 3 is an isometric view of the waste disposal machine from the right side, partially cut away to show some internal details, including a sieve element.

As shown in FIGS. 1 to 3, the waste disposal apparatus 2 includes a cabinet 4 with side panels 6 and two doors 8 forming the front part of the cabinet. The top side of the cabinet is closed by an inclined top cover 10 having a waste inlet 11 that is closed by a hinged lid 12. Operating controls 13 are provided on a front part of the cabinet 4.

Within the cabinet there is provided a decomposition chamber 14 having a four-sided upper part 14*a* and a substantially semi-cylindrical lower part 14*b*. This decomposition chamber 14 is preferably made from a polymeric material, for example polyethylene, for example by rotational moulding.

Located within the decomposition chamber 14 is a semi-cylindrical sieve element 16, comprising a perforated wall or a mesh plate. This is usually made of thin stainless steel plate (typically with a thickness of about 0.9 mm). The perforations or holes in this sieve element 16 are designed to allow water and other liquids to pass through into the lower part 14*b* of the decomposition chamber, while retaining bulky waste materials in the upper part 14*a* of the decomposition chamber. The water and other materials that drain through the sieve element 16 collect in a sump 17 in the lower part 14*b* of the decomposition chamber.

A stirrer device 18 is provided in the decomposition chamber 14 for stirring the contents of the chamber. The stirrer device 18 includes a number of paddles 20 attached by arms 22 to a horizontal shaft 24. The shaft is mounted for rotation in bearings 26 on opposite sides of the chamber 14. One end of the shaft 24 extends through the side of the chamber and is attached to a sprocket 28, as shown in FIG. 3. The stirrer device 18 is driven by an electric motor 30 in the lower part of the cabinet 4 via a gearbox 31 and a drive chain 32.

The hinged lid 12 serves as a closure member that may be opened to allow access to the decomposition chamber 14 through the waste inlet 11, or closed to seal the decomposition chamber 14. The lid 12 and the top cover 10 are preferably made from a polymeric material, for example polyethylene, preferably by rotational moulding.

The top cover 10 may include a locking device (not shown), for example an electrically actuated latching bolt, for locking the lid 12 in a closed condition. Controls 13 for controlling operation of the waste disposal apparatus are provided on the front part of the cabinet above the doors 8.

Concealed within the cabinet 4 behind one of the doors 8 is a compartment for receiving a container of working fluid (not shown). The container is preferably a bag-in-box type, having a sealed bag of fluid supported by a surrounding box or carton and having a tap or valve through which working fluid can be drawn from the bag. The working fluid includes a blend of bacteria, free enzymes and plant extracts, which are effective to promote aerobic decomposition of the waste materials including food waste, oils and greases, and which help to eliminate odours.

Alternatively, or in addition, the microorganisms required for the aerobic decomposition process may be added directly to decomposition chamber 14 through the waste inlet 11. In one preferred embodiment, the microorganisms are added in the form of moulded polymer chips, wherein the microorganisms are embedded within the polymeric material of the polymer chips. The chips do not pass through the sieve element 16, which ensures that the microorganisms are retained within the decomposition chamber and are not washed away with the drain liquid. The chips also allow air to mix with the food waste as the paddles 20 rotate, which speeds up the aerobic digestion process.

Figure 4:
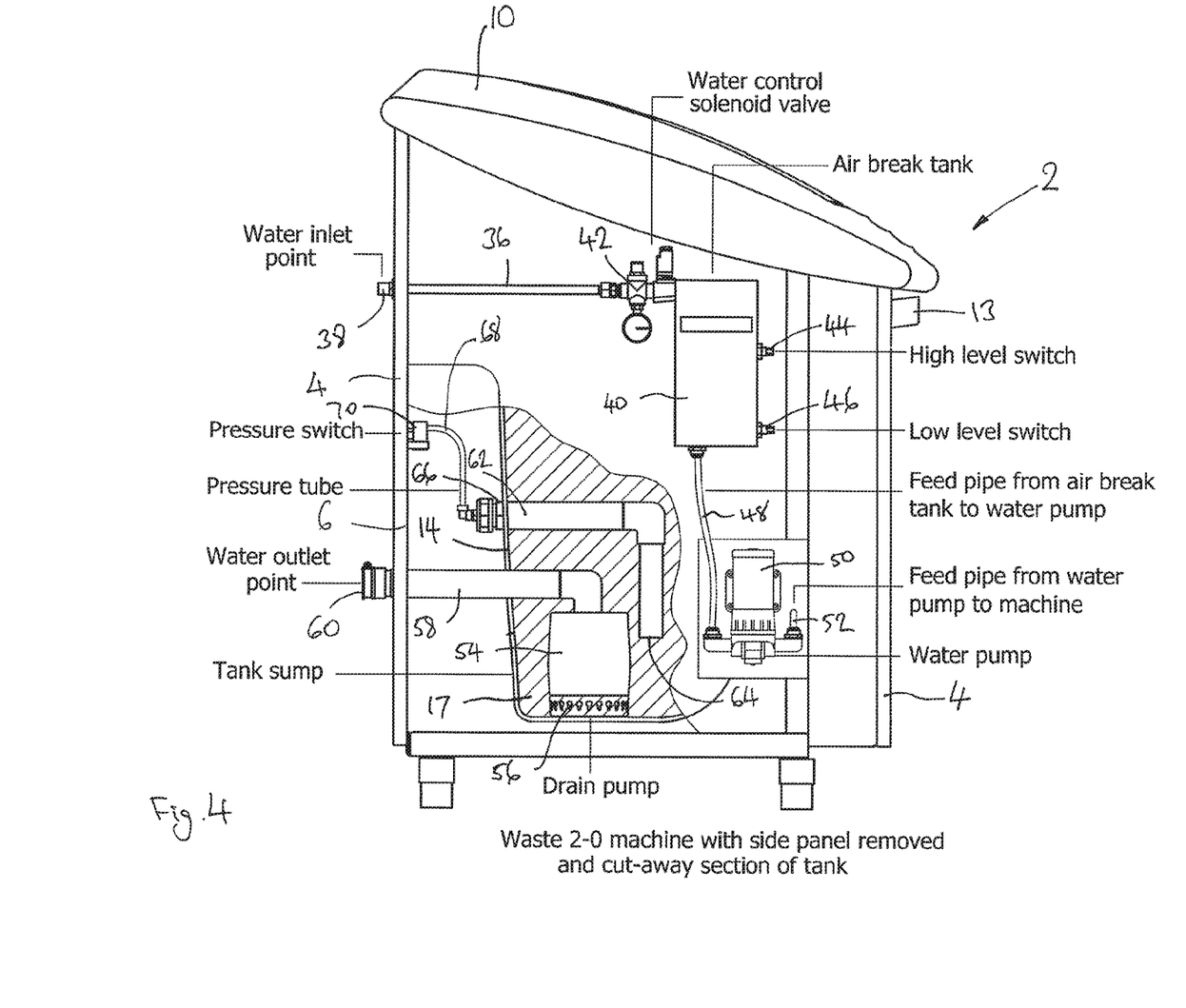
FIG. 4 is a side view of the waste disposal machine from the left side, with a side panel removed and partially cut away to show some internal details.

The main components of a water supply and drainage system are shown in FIG. 4. The system includes a water inlet pipe 36 that delivers water from a water inlet point 38 to an air break tank 40. The flow of water through the pipe 36 is controlled by a solenoid valve 42 upstream of the air break tank 40, according to signals received from a high level switch 44 and a low level switch 46, both of which are located within the tank 40. The solenoid valve 42 opens when the level of water in the tank 40 falls below the low level switch 46 and closes when the level of water in the tank reaches the level of the high level switch 44. The valve 42 is therefore configured to maintain the level of water in the tank 40 between upper and lower levels defined by the positions of the high and low level switches 44, 46.

The air break tank 40 is connected by an inlet feed pipe 48 to a water pump 50, which is configured to feed water through a feed pipe 52 to the decomposition chamber 14, where the water is sprayed onto the waste food products in the chamber.

A drain pump 54 is provided in the sump 17 in the lower part of the decomposition chamber 14. The drain pump 54 has inlet openings 56 near the bottom of the sump 17 and an outlet pipe 58 that extends through the rear side panel 6 of the cabinet 4 to a water outlet point 60. In operation, the drain pump 54 can be actuated to pump a mixture of water and digested food products from the sump 17 of the decomposition chamber 14 to the outlet point 60, from where it can be discharged into a drain.

The waste disposal apparatus 2 includes a level sensing system for sensing the level of liquid in the sump 17 of the decomposition chamber 14. The level sensing system includes a pressure tube 62 that passes horizontally through the side wall of the decomposition chamber 14 and then extends vertically downwards, having an open end 64 that is located within the sump 17 at a predetermined distance above the floor of decomposition chamber 14. A second end 66 of the pressure tube 62 is connected via a pressure line 68 to a pressure switch 70, which is sealed to prevent gases entering or leaving the pressure tube 62 through the pressure line 68.

In use, when the liquid level in the sump 17 is below the open end 64 of the pressure tube 62, the gas pressure in the pressure tube 62 will be substantially equal to the gas pressure in the decomposition chamber 14, which is normally approximately atmospheric pressure. However, when the level of liquid in the decomposition chamber 14 rises above the open end 64 of the pressure tube 62 the gas in the pressure tube 62 will be compressed, increasing the pressure sensed by the pressure switch 70. The pressure switch 70 senses when the pressure rises above a predetermined value, indicating that the liquid in the sump 17 has reached a predetermined depth.

Figure 5:
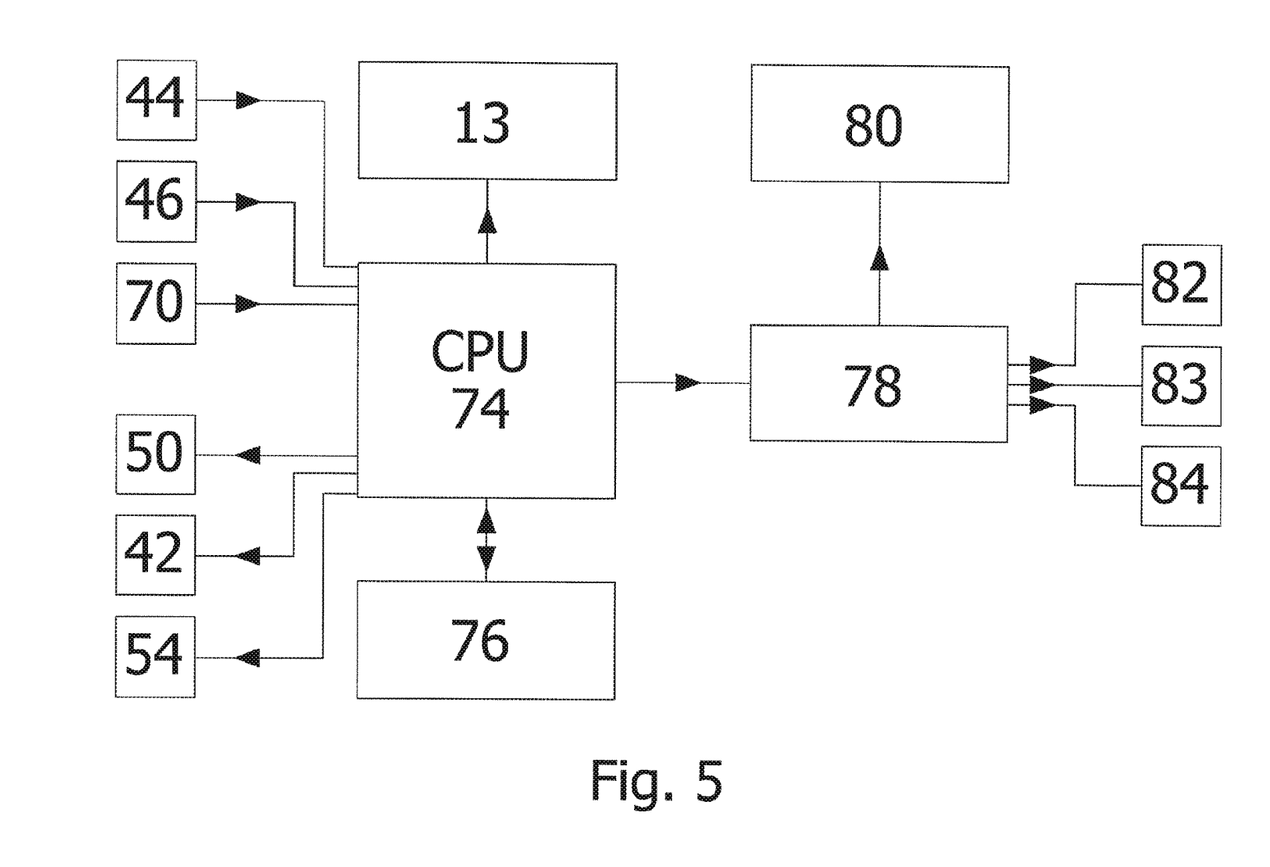
FIG. 5 is a schematic diagram illustrating the main components of a control system for controlling operation of the machine and sensing the quantity of waste materials processed by the machine.

The pressure switch 70, the high and low level switches 44, 46, the water control solenoid valve 42, the water pump 50 and the drain pump 54 are connected to a control system 72 shown schematically in FIG. 5. The control system 72 may also include numerous other sensors, switches and control devices including, for example, devices for controlling and sensing operation of the motor 30, temperature sensors, heater controls, devices for controlling the dispensing of the working fluid, and so on. These other devices are conventional and so will not be described in detail.

The control system 72 includes a central processing unit (CPU) 74, which is connected to receive control signals from the high level switch 44, the low level switch 46 and the pressure switch 70. It is also connected to send control signals to the inlet valve 42, the feed pump 50 and the drain pump 54 to control operation of those devices. The CPU 74 is also connected to receive control signals from the operator controls 13.

The CPU 74 is connected to a memory unit 76, in which operating and control data is stored. The CPU 74 is also connected to an output interface 78, which controls operation of a display device 80, and transmits output data to a wireless transmitter 82, a Bluetooth® connector, a data router 83 and/or a socket 84 for a wired connection, allowing output data to be transferred to an external device (for example, a laptop or tablet computer).

The control system 72 controls operation of the waste disposal apparatus 2 according to signals received from the operator controls 13 and from various sensors including (but not limited to) the high level and low level switches 44, 46 and the pressure switch 70. The control system 72 can be programmed to control all components of the waste disposal apparatus 2, including the motor 30, heaters and so on. Many of these control operations are conventional and will not be described in detail.

The present invention is concerned particularly with the control and monitoring of the water flow system, components of which are shown in FIGS. 4 and 5. These aspects of the control system will be described with reference to FIGS. 6a and 6b.

Figure 6A:
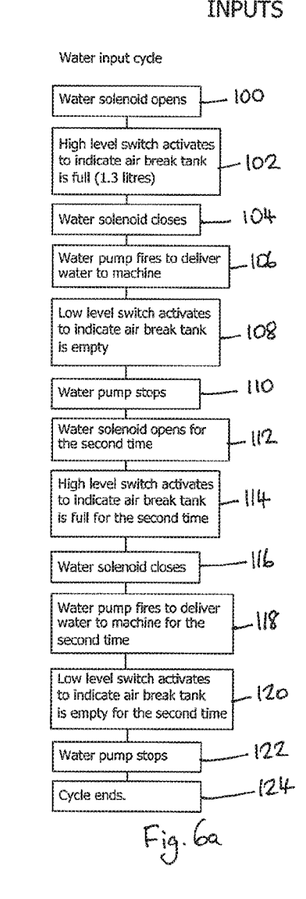
FIGS. 6*a* to 6*d* are flow diagrams showing some important steps in a method of controlling operation of the apparatus.
Figure 6B:
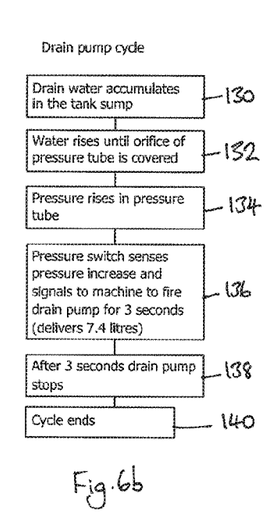

The control system 72 controls operation of a water input cycle and a drain pump cycle, as illustrated in FIGS. 6a and 6b. At the start of the water input cycle (FIG. 6a) the CPU 74 sends an "open" signal to the water control valve 42, which then opens allowing water to flow into the air break tank 40. When the level of water in the tank 40 reaches the high level switch 44 the switch 44 transmits a "stop" signal to the CPU 74 indicating that the tank 40 is full (step 102). In this embodiment the tank 40 has a capacity of 1.3 litres. The CPU 74 then sends a "close" signal to the water control valve 42, shutting off the water supply (step 104).

After shutting off the water supply the CPU 74 sends a "go" signal to the feed pump 50, which then pumps water from the air break tank 40 to the decomposition chamber 14 (step 106). The level of water in the tank 40 falls and when the water level reaches the low level switch 46 the switch 46 sends a control signal to the CPU 74, indicating that the tank 40 is empty (step 108). The CPU 74 then sends a "stop" signal to the feed pump 50, which stops pumping (step 110).

This process is then repeated: the water control valve 42 opens (step 112), the high level switch 44 senses that the tank 40 is full (step 114), the water control valve closes (step 116), the feed pump 50 delivers the water to the decomposition tank 50 (step 118), the low level switch 46 senses that the tank 40 is empty (step 120), and the feed pump 50 stops (step 122). The water input cycle therefore runs twice, after which the cycle stops (step 124).

As indicated above, the air break tank 40 has a capacity (between the high and low level switches 44, 46) of 1.3 litres. The tank 40 is emptied twice during the water input cycle, thus delivering 2.6 litres of water to the decomposition chamber 14. During normal operation, the water input cycle is triggered at regular time intervals, for example every seven minutes. The water input cycle is also triggered every time the machine lid 12 is opened and closed, on the assumption that food waste will have been placed in the decomposition chamber 14 while the lid was opened. Optionally, the machine may be programmed to enter an "energy saving" mode if the lid 12 has not been opened for an extended period, for example, six hours. In this "energy saving" mode, the water input cycle may be triggered less frequently, for example every twenty minutes. Opening and closing the lid 12 causes the machine to revert to its normal operating mode.

The steps of the drain pump cycle are illustrated in FIG. 6b. During operation of the waste disposal apparatus 2, the drain water comprising water and digested food waste flows through the sieve element 16 from the upper part of the decomposition chamber 14 into the sump 17, where it collects (step 130). The level of drain water in the sump 17 gradually rises until it reaches the end of the pressure tube 62 (step 132). As the drain water rises further the pressure of gas trapped within the pressure tube 62 increases (step 134). When the pressure reaches a predetermined value this is sensed by the pressure switch 70, which sends a signal to the CPU 74, which then sends a "go" signal to the drain pump 54 (step 136). The drain pump 54 operates for three seconds, pumping a known quantity of drain water (in this case 7.4 litres) from the sump 17 to the water outlet point 60. After three seconds the CPU 74 sends a "stop" signal to the pump 54, which stops pumping (step 138) and the drain pump cycle ends (step 140).

Figure 6C:
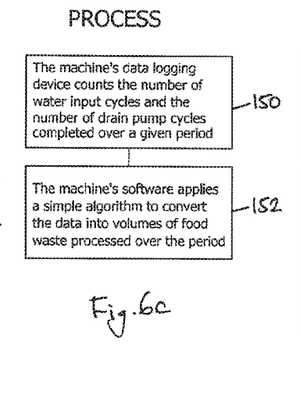

The waste disposal apparatus 2 operates a data logging process to log water usage. The process is illustrated in FIG. 6c. The CPU 74 provides a data logging function in which the number of water input cycles and the number of drain pump cycles are logged over a given period (for example a week) and stored in the memory unit 76 (step 150). The CPU 74 then calculates the mass of food waste processed over the given period using an algorithm (step 152). The algorithm is described in more detail below.

When the mass of food waste processed has been calculated this information is stored in the memory unit 76 and/or delivered via the output interface 78 to an output device, for example a display device 80. The data may also be transferred to an external device wirelessly via the wireless transmitter 82, or through the internet via the data router 83, or through a wired connection via socket 84.

Figure 6D:
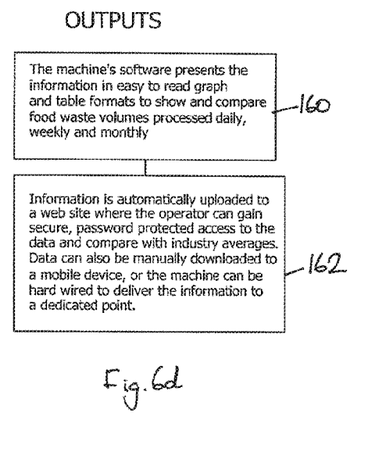

As illustrated in FIG. 6d, the machine software may present the waste processing information in graph and/or table formats allowing the user to compare quantities of food waste processed daily, weekly or monthly (step 160). This information may be automatically uploaded to a website where the operator can gain secure, password protected access to the data for comparison with industry averages. The data can also be downloaded to a mobile device, or the machine can be hardwired to deliver the information to a dedicated access point (step 162).

The algorithm used to determine the mass of food waste processed by the waste disposal apparatus will now be described.

It is known that the average water content of food waste is approximately 70%. It is also known that all of the water present in the food waste processed by the waste disposal apparatus will be discharged through the drain and it has been determined that the drain water discharged from the waste disposal apparatus contains an average of approximately 5% suspended solids. It is therefore possible to calculate the quantity of food waste processed by the machine by measuring the volume of water discharged and subtracting the volume of water fed to the apparatus. The weight of food processed by the machine can then be determined from the calculated volume of processed food waste.

It can thus be determined that the weight of food waste processed by the waste disposal apparatus is given by the algorithm:

$$W=(VD-VF) \div k$$

Where:
W=weight of food waste processed in kg
VD=total volume of drain liquid drained from the decomposition chamber in litres
VF=total volume of feed water supplied to the decomposition chamber in litres
k=a factor derived from the average water content of food waste and the proportion of suspended solids in the drain liquid discharged from the decomposition chamber. We have found that the factor k generally has a value in the range 0.7 to 0.8 and is typically about 0.75.

The total volume of drain liquid drained from the decomposition chamber, and the total volume of feed water supplied to the decomposition chamber, can be determined in any suitable manner. However, our preferred method of sensing these quantities is based on counting the number of times the feed pump and the drain pump are fired within the relevant time period. If the volumes of liquid pumped by each of these pumps each time they are fired are known, the total volumes of drain liquid and feed water can be determined simply by multiplying the pump volumes by the number of firings.

The weight of food waste processed by the waste disposal apparatus can then be determined using the algorithm:

$$W=(Vd \times Nd)-(Vf \times Nf)) \div k$$

Where:
W=weight of food waste processed in kg
Vd=drain pump volume (per firing) in litres
Nd=number of drain pump firings
Vf=volume of water feed (per firing) in litres
Nf=number of feed pump firings
k=a factor, as described above.

If the factor k is taken to be equal to 0.75, this algorithm can be simplified to:

$$W((Vd \times Nd)-(Vf \times Nf)) \div 0.75$$

EXAMPLE

In the specific embodiment of the waste disposal apparatus described above, the following are known factors:
1. The waste disposal apparatus is programmed to deliver 2.6 litres of water into the decomposition chamber each feed cycle. Thus, the feed pump volume Vf=2.6 litres.
2. The drain pump discharges 7.4 litres of drain water each time it fires. Thus, the drain pump volume Vd=7.4 litres.

It is also known that food waste contains an average of 70% water, and the suspended solids present in the drain water discharged from the waste disposal apparatus account for 5% of the fluid volume, giving a value for the factor k of 0.75.

For example, if the number of feed pump firings Nf=166 and the number of drain pump firings Nd=68, then the weight of food waste processed is:

$$W=((7.4 \times 68)-(2.6 \times 166)) \div 0.75$$

Therefore, in this example, W=95 kg

In an embodiment the waste disposal apparatus incorporates software into the food waste digester machine which counts the number of drain pump firings, counts the number of inlet water solenoid openings and applies the above algorithm to calculate the volumes of food waste passed through the food waste digester machine. The information can be stored ready for download by the operator or site manager, or it can be conveyed wirelessly to the appropriate person.

The invention claimed is:

1. A waste disposal apparatus for disposing of waste materials using aerobic decomposition, the apparatus comprising a decomposition chamber, a waste inlet configured to admit waste materials into the decomposition chamber, a water feed system configured for supplying feed water to the decomposition chamber, a drain system configured for draining drain liquid from the decomposition chamber, a sensing system configured to sense a volume VF of feed water supplied to the decomposition chamber and a volume VD of drain liquid drained from the decomposition chamber, and a computing device that is configured to determine a weight W of waste material processed by the waste disposal apparatus from the sensed volumes VF and VD using the algorithm W=(VD−VF)÷k where k has a value in the range 0.7-0.8.

2. A waste disposal apparatus according to claim 1, wherein k has a value of 0.75.

3. A waste disposal apparatus according to claim 2, wherein the drain system comprises a drain pump, and wherein the volume VD of drain liquid drained from the decomposition chamber is determined by sensing the number of times Nd the drain pump is fired and multiplying this value by the drain pump volume Vd.

4. A waste disposal apparatus according to claim 3, wherein the drain system comprises a level sensing device that senses an accumulation of drain liquid in the decomposition chamber, and wherein the drain pump is configured to fire when the accumulation of drain liquid reaches a predetermined level, the drain pump volume Vd being regulated by the volume of the accumulation of drain liquid when the drain pump is fired.

5. A waste disposal apparatus according to claim 1, wherein the water feed system comprises a feed pump, and wherein the volume VF of feed water supplied to the decomposition chamber is determined by sensing the number of times Nf the feed pump is fired and multiplying this value by the feed pump volume Vf.

6. A waste disposal apparatus according to claim 5, wherein the water feed system comprises a water tank from which feed water is drawn by the feed pump, wherein the feed pump volume Vf is regulated by the volume of the water tank.

7. A waste disposal apparatus according to claim 6, wherein the water tank comprises high and low water level sensors, and wherein water is supplied to the water tank via a valve that opens and closes in response to signals received from the high and low water level sensors.

8. A waste disposal apparatus according to claim 1, further comprising a control system that is configured to receive signals from the sensing system and control operation of the water feed system and the drain system in response to signals received from the sensing system.

9. A waste disposal apparatus according to claim 8, wherein the control system comprises a data storage device for storing data relating to operation of the waste disposal apparatus.

10. A waste disposal apparatus according to claim 8, wherein the control system comprises an output device for providing output data relating to operation of the waste disposal apparatus.

11. A method of disposing of waste materials using aerobic decomposition, the method comprising loading waste materials into a decomposition chamber, supplying feed water to the decomposition chamber, draining drain liquid from the decomposition chamber, sensing a volume VF of feed water supplied to the decomposition chamber and a volume VD of drain liquid drained from the decomposition chamber, and determining a weight W of waste material processed by the waste disposal apparatus from the sensed volumes VF and VD using the algorithm W=(VD−VF)÷k where k has a value in the range 0.7-0.8.

12. A method according to claim 11, wherein k has a value of 0.75.

13. A method according to claim 11, wherein the step of sensing the volume VD of drain liquid comprises determining the volume VD of drain liquid drained from the decomposition chamber by sensing the number of times Nd a drain pump is fired and multiplying this value by the drain pump volume Vd.

14. A method according to claim 11, further comprising sensing an accumulation of drain liquid in the decomposition chamber, and firing the drain pump when the accumulation of drain liquid reaches a predetermined level, the drain pump volume Vd being regulated by the volume of the accumulation of drain liquid when the drain pump is fired.

15. A method according to claim 11, wherein the step of sensing the volume VF of feed water supplied to the decomposition chamber comprises determining the volume VF of feed water supplied to the decomposition chamber by sensing the number of times Nf a feed pump is fired and multiplying this value by the feed pump volume Vf.

16. A method according to claim 15, wherein the step of supplying feed water to the decomposition chamber comprises drawing feed water from a water tank using the feed pump, and regulating the feed pump volume Vf by the volume of the water tank.

17. A method according to claim 16, further comprising supplying feed water to the water tank via a valve and controlling the valve so that it opens and closes in response to signals received from high and low water level sensors in the water tank.

18. A method according to claim 11, further comprising receiving signals from a sensing system and controlling operation of a water feed system and a drain system in response to signals received from the sensing system.

19. A method according to claim 11, further comprising storing data relating to operation of the waste disposal apparatus in a data storage device.

20. A method according to claim 11, further comprising providing output data relating to operation of the waste disposal apparatus.

21. A method according to claim 11, wherein the waste materials are disposed of by aerobic decomposition, in which the waste materials are placed in the decomposition chamber, a working fluid that comprises a blend of bacteria, free enzymes and plant extracts is applied to the waste materials, the waste materials are stirred to encourage aerobic decomposition thereof, and decomposed waste materials are discharged from the chamber.

22. A method according to claim 21, in which the waste materials are waste food products.

23. A method according to claim 11, wherein the method is implemented using an apparatus comprising a decomposition chamber, a waste inlet configured to admit waste materials into the decomposition chamber, a water feed system configured for supplying feed water to the decomposition chamber, a drain system configured for draining drain liquid from the decomposition chamber, a sensing system configured to sense a volume VF of feed water supplied to the decomposition chamber and a volume VD of drain liquid drained from the decomposition chamber, and a computing device that is configured to determine the weight of waste material processed by the waste disposal apparatus from the sensed volumes VF and VD using said algorithm $W=(VD-VF) \div k$ where k has a value in the range 0.7-0.8.

24. A waste disposal apparatus for disposing of waste materials using aerobic decomposition, the apparatus comprising:
- a decomposition chamber;
- a waste inlet that opens into the decomposition chamber and that is adapted to admit associated waste materials to be decomposed into the decomposition chamber;
- a water inlet and a drain liquid outlet;
- a water tank in fluid communication with the water inlet;
- a water pump in fluid communication with both the water tank and the decomposition chamber and adapted to pump water from the water tank to the decomposition chamber;
- a drain pump in fluid communication with both the decomposition chamber and the drain liquid outlet and adapted to pump drain liquid from the decomposition chamber to the drain liquid outlet;
- a water feed sensor that provides information related to a volume VF of water supplied to the decomposition chamber from the water tank by the water pump;
- a drain liquid sensor that provides information related to a volume VD of drain liquid pumped by the drain pump from the decomposition chamber to the drain liquid outlet;
- a computing device that is configured to determine a weight W of the associated waste materials processed by the waste disposal apparatus based upon the volume VF of water supplied to the decomposition chamber from the water tank by the water pump and based upon the volume VD of drain liquid pumped by the drain pump from the decomposition chamber to the drain liquid outlet, wherein said computing device calculates said weight W of the associated waste materials according to: $W=(VD-VF) \div k$ where k has a value in the range 0.7-0.8.

25. The waste disposal apparatus as set forth in claim 24, wherein the drain liquid sensor comprises a drain liquid level sensor located in said decomposition chamber that senses a select volume of drain liquid accumulated in the decomposition chamber, and wherein the drain pump operates to pump said select volume of drain liquid from the decomposition chamber to the drain liquid outlet when the drain liquid level sensor senses the select volume of drain liquid in the decomposition chamber.

26. The waste disposal apparatus as set forth in claim 24, wherein the water feed sensor comprises a water level sensor located in the water tank that senses a select volume of water contained in the water tank, and wherein the water pump operates to pump the select volume of water from the water tank to the decomposition chamber.

* * * * *